United States Patent [19]
Bymaster et al.

[11] Patent Number: 6,043,258
[45] Date of Patent: Mar. 28, 2000

[54] METHOD FOR TREATING DISRUPTIVE BEHAVIOR DISORDERS WITH XANOMELINE

[75] Inventors: Franklin P Bymaster, Brownsburg; Harlan E Shannon, Carmel, both of Ind.

[73] Assignee: Eli Lilly and Company, Indianapolis, Ind.

[21] Appl. No.: 09/202,552

[22] PCT Filed: Jul. 28, 1997

[86] PCT No.: PCT/US97/13186

§ 371 Date: Dec. 16, 1998

§ 102(e) Date: Dec. 16, 1998

[87] PCT Pub. No.: WO98/05325

PCT Pub. Date: Feb. 12, 1998

Related U.S. Application Data

[60] Provisional application No. 60/022,919, Aug. 1, 1996.
[51] Int. Cl.[7] .................................................. A61K 31/44
[52] U.S. Cl. .............................................. 514/342
[58] Field of Search ............................................. 514/342

[56] References Cited

U.S. PATENT DOCUMENTS

| | | | |
|---|---|---|---|
| 5,041,455 | 8/1991 | Sauerberg et al. | 514/342 |
| 5,043,345 | 8/1991 | Sauerberg et al. | 514/342 |
| 5,328,923 | 7/1994 | Sauerberg et al. | 514/340 |
| 5,328,924 | 7/1994 | Sauerberg et al. | 514/340 |
| 5,488,056 | 1/1996 | Bodick et al. | 514/305 |
| 5,708,014 | 1/1998 | Bodick et al. | 514/340 |

FOREIGN PATENT DOCUMENTS

| | | |
|---|---|---|
| 0 307 142 A1 | 3/1989 | European Pat. Off. . |
| 0 384 288 A2 | 8/1990 | European Pat. Off. . |
| 0 709 094 A2 | 5/1996 | European Pat. Off. . |
| 0 723 781 A2 | 7/1996 | European Pat. Off. . |
| WO 94/20495 | 9/1994 | WIPO . |
| WO 94/29303 | 12/1994 | WIPO . |
| WO 95/05174 | 2/1995 | WIPO . |
| WO 95/17185 | 6/1995 | WIPO . |
| WO 96/13168 | 5/1996 | WIPO . |

OTHER PUBLICATIONS

Rapaport, et al., *Biol. Psychiatry,* 29, 658–664 (1991).
Katzung, B.G., *Basic & Clinical Pharmacology,* (Appleton & Lange, Norwald), 90–94 (1995).
Sauerberg, et al., *J. Med. Chem.,* 35, 2274–2283 (1992).

*Primary Examiner*—William R. A. Jarvis
*Attorney, Agent, or Firm*—David M. Stemerick; MaCharri R. Vorndran-Jones

[57] ABSTRACT

This invention relates to the use of xanomeline for the treatment of Disruptive Behavior Disorder and Attention Deficit Hyperactivity Disorder.

14 Claims, No Drawings

METHOD FOR TREATING DISRUPTIVE BEHAVIOR DISORDERS WITH XANOMELINE

This application is a 371 of PCT/US97/13186, filed Jul. 28, 1997 and claims priority to provisional application No. 60/022,919, filed Aug. 1, 1996.

This invention provides a method for using 3-(4-hexyloxy-1,2,5-thiadiazol-3-yl)-1,2,5,6-tetrahydro-1-methylpyridine, (hereinafter referred as "xanomeline"), for the treatment of disruptive behavior disorders.

A subject suffering from a Disruptive Behavior Disorder exhibits a consistent pattern of inattention and/or hyperactivity-impulsivity that is more frequent and severe than is typically observed in individuals at a comparable level of development. Such subjects must suffer clear evidence of interference with developmentally appropriate social, academic, or occupational functioning. Individuals suffering from a Disruptive Behavior Disorder may fail to give close attention to details or may make careless mistakes in schoolwork or other tasks. Individuals often have difficulty sustaining attention in tasks or play activities and find it difficult to persist with tasks to completion. Tasks that require sustained mental effort are experienced as unpleasant and markedly aversive. As a result, these individuals typically avoid or have a strong dislike for activities that demand sustained self-application and mental effort or that require organizational demands or close concentration (e.g., homework or paperwork). Individuals suffering from a Disruptive Behavior Disorder have difficulty in common situations that require sustained attention, for example listening to a classroom teacher, doing class assignments, listening to or reading lengthy materials, or working on repetetive tasks. The condition manifests itself in adolescents and adults as a feeling of restlessness and difficulty engaging in quiet sedentary activities. If untreated, the condition may result in compromised school adjustment and feelings of jitteriness.

Disruptive Behavior Disorders are prevalent conditions afflicting elementary school-age children as well as adolescents and adults. It is estimated that from 3–5% of elementary school-age children suffer from Attention Deficit/Hyperactivity Disorder.

Applicants have discovered that xanomeline, thought to be a muscarinic agonist, can be useful for treating such Disruptive Behavior Disorders. More specifically, the invention provides a method of treating Attention Deficit/Hyperactivity Disorder in a mammal using xanomeline. Further, the present invention provides a method of treating Attention Deficit/Hyperactivity Disorder in a human using xanomeline.

As noted hereinbefore, the compound employed in the method of the present invention is known. Methods of preparing the compound, as well as pharmaceutical formulations containing the compound, are taught by Sauerberg in U.S. Pat. No. 5,043,345 (hereinafter referred to as the "'345 patent") herein incorporated by reference. The '345 patent teaches that xanomeline can be useful for treating Alzheimer's Disease and as stimulants of the cognitive function of the forebrain and hippocampus of mammals. Unlike Alzheimer's Disease, the onset of Attention Deficit/Hyperactivity Disorder is before the age of seven and has many different etiologies. Xanomeline may address a long felt need for new treatments which provide a favorable safety profile and effectively provides relief for the patient or individual suffering from a Disruptive Behavior Disorder.

The presently claimed invention provides a method for treating a Disruptive Behavior Disorder, comprising administering an effective amount of a compound of Formula I:

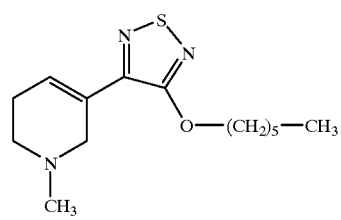

or
a pharmaceutically acceptable salt or solvate thereof to a patient in need of such treatment.

The presently claimed invention provides a method for treating Attention Deficit/Hyperactivity Disorder, comprising administering an effective amount of a compound of Formula I:

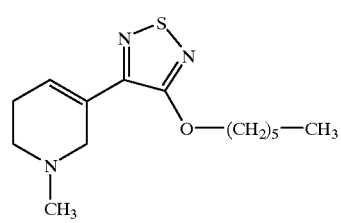

or
a pharmaceutically acceptable salt or solvate thereof to a patient in need of such treatment.

As used herein, the term "Disruptive Behavior Disorder" shall refer to a condition characterized as a Disruptive Behavior Disorder, in the DSM-IV-R. *Diagnostic and Statistical Manual of Mental Disorders, Revised,* 4th Ed (1994) as catagories 314.xx, 312.xx, and 313.xx, . The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic psychological conditions and that these systems evolve with medical scientific progress. Most preferredly the term refers to the DSM-IV-R 314.xx categories. The 314.xx catagories of the DSM-IV-R currently include 314.01, 314.00, and 314.9.

The term "effective amount", as used herein, represents an amount of compound necessary to prevent or treat a human susceptible to or suffering from Disruptive Behavior Disorder following administration to such human. The active compound is effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compound may be administered orally to humans susceptible to or suffering from Disruptive Behavior Disorder, the compound is particularly well suited to be administered transdermally. When the compound is delivered transdermally, it is preferred that the effective amount is from about 10 mg to about 100 mg per day delivery of base compound. It is especially preferred that such patch delivers an effective amount for about one to seven days.

The compound may further be delivered by a variety of other pharmaceutically accepted routes including, but in no way limited to parenterally, subcutaneous, intranasal, intramuscular and intravenous routes. Such formulations may be designed to provide delayed or controlled release using formulation techniques which are known in the art.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

The compounds employed in the invention are not believed to act via the GABA/benzodiazepine, serotonin, or dopamine receptor systems in humans. Rather, the activity of the present compound as a treatment for Disruptive Behavior Disorder is believed to be based upon modulation of muscarinic cholinergic receptors. However, the mechanism by which the present compounds function is not necessarily the mechanism stated supra., and the present invention is not limited by any mode of operation.

In addition, 3-(4-hexyloxy-1,2,5-thiadiazol-3-yl)-1,2,5,6-tetrahydro-1-methylpyridine has been found to have a favorable profile of activity in a number of in vitro binding assays, designed to measure the degree of binding to neural receptors.

Xanomeline has been studied using accepted pharmacological methods such as oxotremorine-M verses N-methylscopolamine binding studies (Freedman et al. *Br. J. Pharmacology*, 93:437–445 (1988). Xanomeline inhibited the binding of $^3$H-oxotremorine-M with an inhibition constant (Ki) of 2 nM. The binding of the muscarinic m1 antagonist ligand, $^3$H-pirenzepine, to m1 receptors in hippocampus and $^3$H-quinuclidinyl benzilate to m2 receptors in brain stem was inhibited with Ki values of 5 and 24 nM, respectively.

Muscarinic agonists stimulate the formation of cAMP up to 10 fold in CHO m4 cells treated with pertussisi toxin and the pharmacology is consistent with the mediation by m4 receptors. Eckols K. *Soc. Neurosci Abstr.*, 21:2040 (1995). In this assay, xanomeline efficaciously and potently stimulated the formation of CAMP. Such studies suggest that xanomeline predominantly activates m1 and m4 receptors. Further, accepted pharmacological studies have shown that xanomeline is active at the D2 receptor subtype.

Xanomeline has a moderate affinity for $5HT_{2C}$ and $5HT_{1D}$ receptor subtypes as indicated by Ki values of 120 and 180 nM respectively.

The clinical benefit of using xanomeline for the treatment of Disruptive Behavior and/or Attention Deficit Hyperactivity disorder can be supported by the following examples. These examples are not intended to limit the scope of the invention in any way.

EXAMPLE 1

Human Clinical Trials

The activity of 3-(4-hexyloxy-1,2,5-thiadiazol-3-yl)-1,2,5,6-tetrahydro-1-methylpyridine for treating or alleviating Disruptive Behavior Disorder can be demonstrated by human clinical trials. The study was designed as a double-blind, parallel, placebo-controlled multicenter trial. The subjects were randomized into four groups, placebo and 25, 50, and 75 mg tid of test compound. The dosages were administered orally with food. Subjects were observed at four visits to provide baseline measurements. Visits 5–33 served as the treatment phase for the study.

During the visits, subjects are observed for behavioral, social interaction, intellectual, and concentration abilities.

Treatment groups are compared with respect to the number and percent of subjects who ever had the symptom during the double-blind portion of the study (visits 5 through 33), at a severity that was worse than during the baseline visits (1 through 4).

We claim:

1. A method for treating Disruptive Behavior Disorder comprising administering to a mammal in need of such treatment, an effective amount of a compound of Formula I:

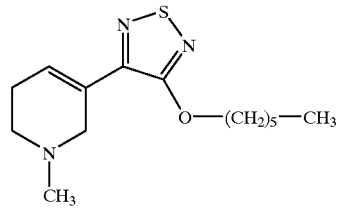

or a pharmaceutically acceptable salt thereof.

2. A method of claim 1 wherein the effective amount is from 1 mg/kg to about 100 mg/kg per day.

3. A method of claim 2 wherein the effective amount is from about 50 mg/kg to about 100 mg/kg per day.

4. A method of claim 1 wherein the effective amount is delivered using a transdermal patch.

5. A method of claim 4 wherein the transdermal patch delivers from about 10 to about 100 mg of base compound per day.

6. A method of claim 5 wherein the transdermal patch delivers an effective amount for one (1) to seven (7) days.

7. A method of claim 1 wherein the mammal is a human.

8. A method for treating Attention Deficit/Hyperactivity Disorder comprising administering to a mammal in need of such treatment, an effective amount of a compound of Formula I:

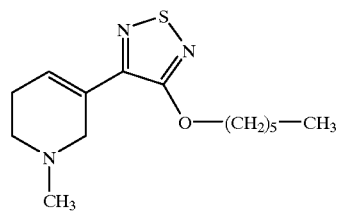

or a pharmaceutically acceptable salt thereof.

9. A method of claim 8 wherein the mammal is a human.

10. A method of claim 9 wherein the effective amount is from 1 mg/kg to about 100 mg/kg per day.

11. A method of claim 10 wherein the effective amount is from about 50 mg/kg to about 100 mg/kg per day.

12. A method of claim 10 wherein the effective amount is delivered using a transdermal patch.

13. A method of claim 12 wherein the transdermal patch delivers from about 10 to about 100 mg of base compound per day.

14. A method of claim 13 wherein the transdermal patch delivers an effective amount for one (1) to seven (7) days.

* * * * *